(12) United States Patent
Woerlein

(10) Patent No.: US 9,044,269 B2
(45) Date of Patent: Jun. 2, 2015

(54) TWO-PART MEDICAL TRACKING MARKER

(75) Inventor: Swen Woerlein, München (DE)

(73) Assignee: Brainlab AG, Feldkirchen (DE)

( * ) Notice: Subject to any disclaimer, the term of this patent is extended or adjusted under 35 U.S.C. 154(b) by 0 days.

(21) Appl. No.: 13/497,127

(22) PCT Filed: Sep. 30, 2009

(86) PCT No.: PCT/EP2009/062685
§ 371 (c)(1),
(2), (4) Date: Mar. 20, 2012

(87) PCT Pub. No.: WO2011/038759
PCT Pub. Date: Apr. 7, 2011

(65) Prior Publication Data
US 2012/0184839 A1    Jul. 19, 2012

(51) Int. Cl.
*A61B 5/05* (2006.01)
*A61B 19/00* (2006.01)
(Continued)

(52) U.S. Cl.
CPC .................. *A61B 19/54* (2013.01); *A61B 19/08* (2013.01); *A61B 19/081* (2013.01); *A61B 19/38* (2013.01); *A61B 2017/00876* (2013.01); *A61B 2019/5483* (2013.01)

(58) Field of Classification Search
CPC ...... A61B 19/54; A61B 19/08; A61B 19/081; A61B 19/38; A61B 2017/00876; A61B 2019/5483
USPC .......... 600/206, 407–430; 606/1–5, 206–214; 442/118, 334, 361, 414
See application file for complete search history.

(56) References Cited

U.S. PATENT DOCUMENTS 5,979,450 A * 11/1999 Baker et al. ................... 128/849
6,424,856 B1    7/2002 Vilsmeier et al.
(Continued)

FOREIGN PATENT DOCUMENTS

| DE | 296 04 408 | 5/1996 |
| DE | 196 39 615 | 4/1998 |
| WO | 2004/075768 | 9/2004 |

OTHER PUBLICATIONS

International Search Report for International Application No. PCT/EP2009/062685 dated Jun. 25, 2010.

*Primary Examiner* — Sanjay Cattungal
(74) *Attorney, Agent, or Firm* — Tucker Ellis LLP

(57) ABSTRACT

The invention relates to a medical tracking marker (12) for localizing or tracking an object (10) by means of a medical tracking system (30), said marker comprising a first part (1) which is to be fixed on the object (10), and a second part (2) which is to be connected to the first part (1), wherein the first and second parts (1, 2) comprise interconnecting elements (4, 6) which are adapted to provide a positionally determined connection between the first part (1) and the second part (2) while the first part is located under a surgical drape (20) and the second part is located above said surgical drape (20), with the drape (20) placed between the two parts (1, 2). The invention also relates to a method of referencing an object (10) using a medical navigation system, wherein a medical tracking marker such as has been described above is localized or tracked by means of a medical tracking system (30), and wherein the object is registered by means of the first part (1) of the marker (12) in a preliminary referencing step, in particular for imaging purposes, which is later adapted to form a final referencing step for navigation using the second part (2) which has been placed on the first part in a positionally defined, pre-determined manner.

18 Claims, 2 Drawing Sheets

Figure 1:
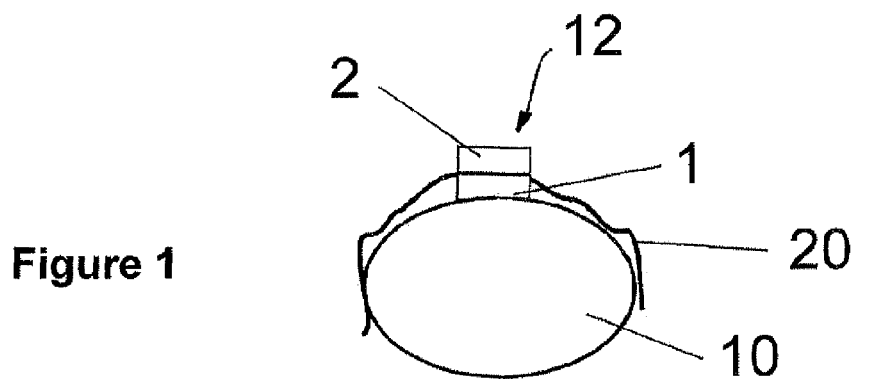

(51) Int. Cl.
  *A61B 19/08* (2006.01)
  *A61B 17/00* (2006.01)

(56) References Cited

U.S. PATENT DOCUMENTS

| | | |
|---|---|---|
| 6,471,172 B1 | 10/2002 | Lemke et al. |
| 6,742,522 B1 * | 6/2004 | Baker et al. .................... 128/849 |
| 2003/0104746 A1 * | 6/2003 | Menzies et al. ................ 442/328 |
| 2006/0025677 A1 | 2/2006 | Verard et al. |
| 2007/0106282 A1 * | 5/2007 | Lavallee ............................ 606/1 |
| 2007/0224903 A1 * | 9/2007 | Chakravarty et al. ......... 442/361 |
| 2008/0285721 A1 | 11/2008 | Dehler |
| 2009/0264709 A1 * | 10/2009 | Blurton et al. ................ 600/206 |

* cited by examiner

TWO-PART MEDICAL TRACKING MARKER

This application is a national phase of International Application No. PCT/EP2009/062685 filed Sep. 30, 2009 and published in the English language.

The present invention relates to a medical tracking marker which is used when an object is to be localized or tracked by means of a medical tracking system, preferably an optical medical tracking system. Such medical tracking markers are known in general for example from DE 196 39 615 A1 and are used in conjunction with a medical navigation system. The above-referenced document discloses a multi-part marker system comprising one part which is to be fixed on the patient and two different marker parts which, alternatively, may be attached to said part for different purposes, for example one fiducial marker for imaging purposes and a second one for tracking purposes. Other known marker systems involve invasively fixing individual markers or a head ring bearing such markers, wherein fixing includes penetrating the bone. Such systems are particularly problematic in pediatrics owing to their size and invasiveness. Another problem to be dealt with concerns the need to drape the patient in order to provide a sterile environment, since the markers must somehow be arranged above the drapes for tracking purposes but fixed below the drapes. In accordance with the prior art, either the drapes are arranged around the markers or the markers penetrate the drapes, both of which methods compromise sterility.

In general, it is the function of a marker to be detected by a marker detection device (for example, a camera or an ultrasound receiver), such that its spatial position (i.e. its spatial location and/or alignment) can be ascertained. Such markers can be active markers. An active marker emits for example electromagnetic radiation and/or waves, wherein said radiation can be in the infrared, visible and/or ultraviolet spectral range. The marker can also however be passive, i.e. can for example reflect electromagnetic radiation from the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and may therefore be referred to as a marker sphere; markers can also, however, exhibit a cornered—for example, cubic—shape or a disk shape.

It is the object of the present invention to provide a medical tracking marker and a method of referencing an object using a medical navigation system by using such a marker, which provide a wide range of application and preserve sterility. This object is achieved by a tracking marker in accordance with claim 1 and a method of referencing an object using a medical navigation system in accordance with claim 13. The sub-claims define advantageous embodiments of the invention.

The tracking marker of the present invention comprises a first part which is to be fixed on the object, and a second part which is to be connected to said first part. The first and second parts comprise interconnecting elements which are adapted to provide a positionally determined connection between the first part and the second part while the first part is located under a surgical drape and the second part is located above said surgical drape, with the drape placed between the two parts.

In other words, the present invention adapts the marker configuration by accepting that draping must take place and by taking the presence of a drape into account in designing the marker. In particular, providing a positionally determined connection between the parts which are "separated" by the drape enables accurate tracking and localizing, while a large degree of freedom is provided in the design with respect to fixing the first part on the object, for example on the patient's skin. In this way, the invention provides an accurate and robust tracking marker technology and excellent sterility conditions.

In one embodiment of the invention, the marker parts are not in direct contact when connected. In particular, their interconnecting elements are not in direct contact with each other. Said interconnecting elements may, when connected, be spaced apart by at least a distance corresponding to the thickness of the surgical drape, wherein the connection bridges said distance. The marker according to the invention may be designed in such a way that the interconnecting elements do not penetrate the drape when connected. The marker parts, when connected, may clamp the drape without penetrating it. One way of establishing such a connection is to use forces which act over a distance, in particular magnetic or electrostatic forces (or fields). In this case, the parts may be provided with two different magnetic or static domains in the connecting area, in particular on each surface involved in the connection, thereby securing a predetermined alignment of the parts which are connected without contacting each other.

On the other hand, a positive connection between the interconnecting elements may be chosen in order to connect the two marker parts, wherein the drape is accommodated between said elements which in particular form a bayonet catch or a quarter-turn fastener.

Another way of connecting the parts involves a frictional engagement between the interconnecting elements, wherein the drape is preferably accommodated between said elements and thus forms a part of the frictional connection.

In another embodiment of the medical tracking marker in accordance with the invention, the first part of said marker is fixed on the object non-invasively, i.e. said first part comprises a non-invasive object connection means which for example adhesively bonds the marker part onto the object or fixes it there by means of adhesive tape. Such non-invasive fixing techniques are particularly suitable for pediatrics or pediatric cranial procedures in which conventional reference systems are ill-suited due to the size of a child's head and the limited rigidity/thickness of the cranial bone. One of the first and second parts, in particular the second part, or both parts may be provided in accordance with the invention with a reflective surface which can be detected by the tracking system, such that at least the second part, but in some instances (where useful) also the first part, may be used for direct tracking purposes.

The method of the present invention is a method of referencing an object using a medical navigation system, wherein a medical tracking marker such as has been described above in various embodiments is localized or tracked by means of a medical tracking system, preferably an optional medical tracking system, and wherein the object is referenced by means of the first part of the marker in a preliminary referencing step, in particular for imaging purposes, which is later adapted to form a final referencing step for navigation using the second part which has been placed on the first part in a positionally defined, predetermined manner.

Thus, referencing and registration are advantageously combined in the method in accordance with the invention.

A navigation system and/or surgical navigation system is understood to mean a system consisting of: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) comprises in particular a processor (CPU), a working memory, advantageously an indicating device (for example, a visual indicating device such as a monitor and/or an audio indicating device such as a loudspeaker) and advantageously a permanent data memory, wherein the data processing device processes navigation data forwarded to it by the receiver and can advantageously output guidance information to a user via the indicating device. The navigation data can be stored in the permanent data memory and for example compared with data which has been stored in said memory beforehand.

With respect to the term "registration", the n-dimensional image of a body is registered when the spatial location of each point of a real object within a space, for example a body part in an operating theatre, is assigned an image data point of an image (CT, MR, . . . ) stored in a navigation system. Determining the position is called "referencing" if it implies informing a navigation system of said position in a reference system of the navigation system.

In one embodiment of the method in accordance with the invention, the adapting step compensates for and takes into account the shift in the position of the marker which occurs when the second part is placed on the first part, and in particular takes into account one or more of the following:
  the thickness of the drape;
  a specific shape of the second part;
  characteristics of or inaccuracies in the system connecting the parts;
  a shift in the skin;
  a movement of the tracking system.

One way of taking such a shift in position into account is to ignore markers which are found to have shifted during the medical navigation.

The invention also relates to a computer program which, when it is running on a computer or is loaded onto a computer, causes the computer to perform a method as described above, and to a computer program storage medium which comprises such a computer program.

With respect to the above, the method in accordance with the invention is in particular a data processing method. The data processing method is preferably performed using technical means, in particular a computer. The computer in particular comprises a processor and a memory in order to process the data, in particular electronically. The calculating steps described are in particular performed by a computer. Steps of defining for example regions or values are in particular steps of determining data within the framework of the technical data processing method, in particular within the framework of a program. Altering steps in particular represent altering the data by means of the computer. Ascertaining steps in particular include retrieving values which are provided at an interface of the computer and have been generated by technical means, such as for example a scanning device. These values are in particular converted by the interface into data which can be processed by the computer.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Such a system can be a computer; a computer can be a data processing device comprising means for executing the computer program elements and/or the program in accordance with the invention. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s). The computer and/or data processing device can in particular constitute a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated in an instrument).

In accordance with another aspect of the invention, it relates to a medical tracking marker for localizing or tracking an object by means of a medical tracking system, said marker comprising a first part which is to be fixed on the object, and a second part which is to be connected to the first part, wherein the first and second parts comprise interconnecting elements which are adapted to provide a positionally determined connection between the first part and the second part, and wherein one of the first and second parts or both parts are trackable by the tracking system, in particular provided with a reflective surface which can be detected by the tracking system. In one embodiment, the first part may be trackable, so that it can—standing alone—be used as a tracking marker. In this aspect of the invention, all of the embodiments described herein and in the claims may be implemented, in particular those dealing with the adaptations for use with a surgical drape and those dealing with the various ways of interconnecting the two parts. This inventive aspect, of course, further relates to and comprises a method as discussed herein, adapted for use with the marker according to said aspect.

Figure 2:
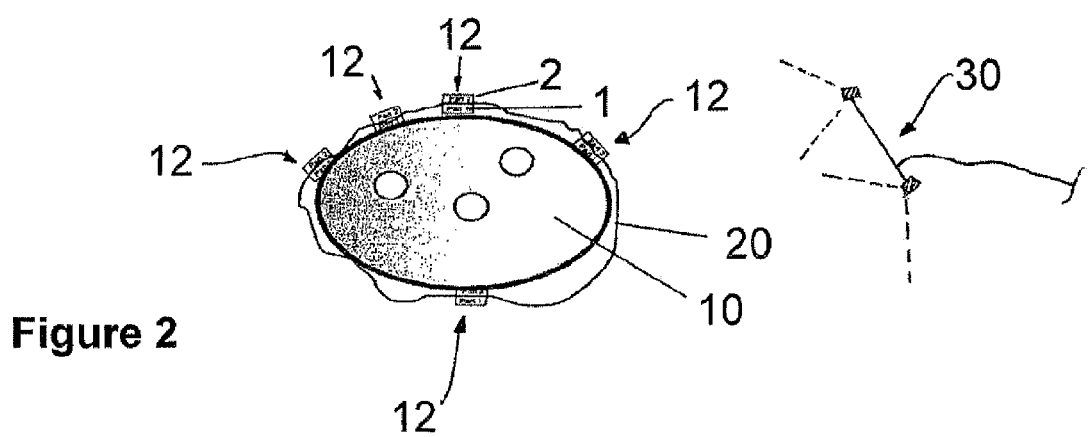
Figure 3:
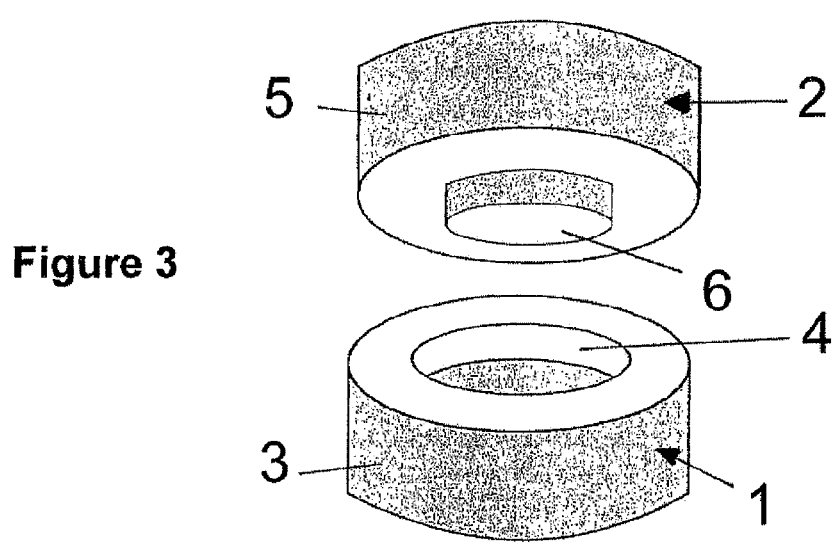
Figure 4:
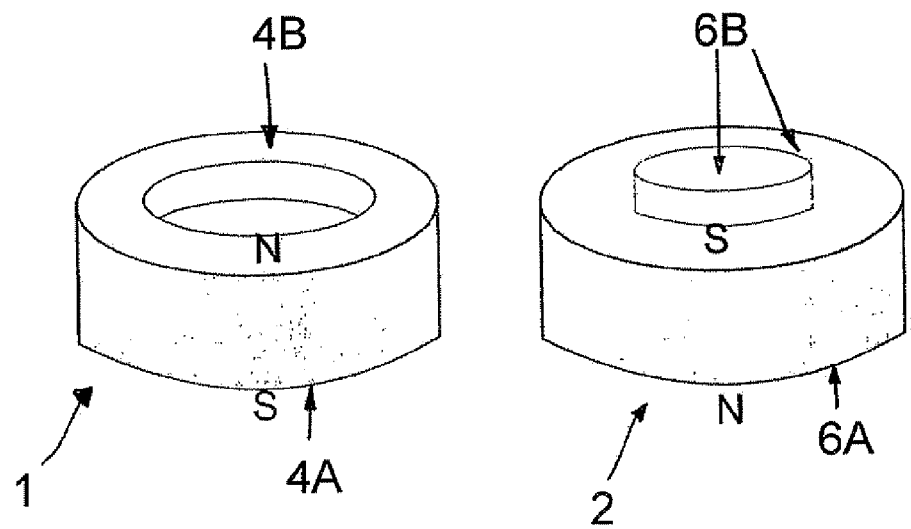

The invention will now be described in more detail by referring to particular embodiments and to the attached drawings. It is to be noted that each of the features of the present invention as referred to here may be implemented separately or in any expedient combination. The drawings show:

FIGS. 1 and 2 an overall arrangement of tracking markers in accordance with the invention, on a sterile draped object;

FIG. 3 a first embodiment of a marker in accordance with the invention;

FIG. 4 a second embodiment of a marker in accordance with the invention; and

Figure 5:
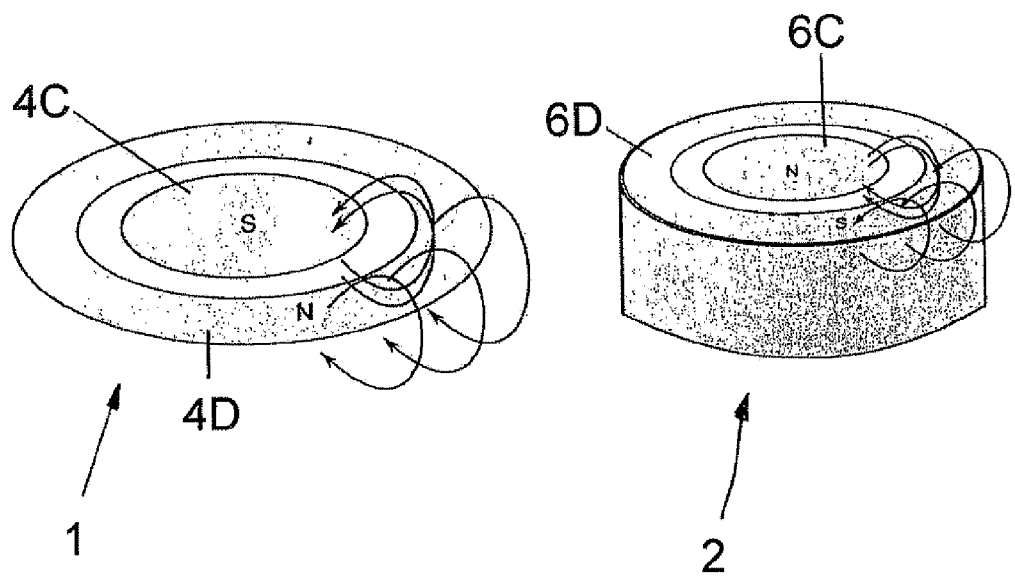

FIG. 5 one variant of a magnetic connection technology for a marker in accordance with the invention.

FIGS. 1 and 2 show the use of markers in accordance with one embodiment of the present invention. The markers bear the reference sign 12 and consist of a first part 1 and a second part 2. The first part 1 is fixedly attached to an object 10 which could be a part of a patient's body. The object 10 is covered with a surgical drape 20 which is accommodated between the parts 1 and 2 of the marker 12. In FIG. 2, the body part 10 has been fitted with a number of markers 12 which are localized and tracked by a tracking system 30 which is shown schematically and usually consists of a mounting and two cameras. The cameras provide a stereoscopic image of the markers 12 and can thus detect their location and the 3D location of the object 10 after a registration procedure.

One embodiment of a marker in accordance with the invention is shown in FIG. 3. The first marker part 1 comprises a body 3 featuring a circular recess 4 on its upper side, while the second part 2 comprises a body 5 featuring a circular extension 6 on the side facing the first part 1. The recess 4 and the extension 6 on the respective sides of the parts 1 and 2 together form the interconnecting elements which serve to fasten the parts 1 and 2 to each other. The extension 6 and the recess 4 are dimensioned in such a way that a frictional engagement between the two elements is provided when a surgical drape is placed between the parts 1 and 2. With respect to this and the following embodiments, it may be noted that the position of the first part 1 with respect to the second part 2 will in any event be known and/or predictable, i.e. predetermined by their design and the known thickness of the surgical drape being used.

The embodiment of FIG. 4 does not employ a frictional engagement but rather magnetic forces. The first part 1 is magnetized in such a way that its magnetic south is on the lower side 4A and its magnetic north is on the upper or connecting side 4B which comprises the recess. The second part 2, by contrast, exhibits its magnetic south on the connecting side 6B and its magnetic north on the opposite side 6A which becomes the upper or outside (reflecting) side of the marker during use. In this embodiment, the recess on the side 4B and the extension on the side 6B mainly serve the purpose of alignment and can be dimensioned in such a way that an alignment is guaranteed when a surgical drape is placed between the sides 4B and 6B when the marker parts 1 and 2 are assembled.

Another way of ensuring an alignment of the two marker parts 1 and 2 is shown in FIG. 5, in which for the sake of clarity only the upper side of the first part 1 is shown on the left. On the upper side shown in FIG. 5, the first part 1 comprises a circular domain 4C which exhibits a magnetic south and forms an inner circle. At a distance from the circle 4C, an outer ring 4D is provided which exhibits a magnetic north polarity, i.e. there are two polarities on the connecting face, namely the circle 4C having a magnetic south polarity and the outer ring 4C having a magnetic north polarity. The second part 2 is designed conversely, with an outer ring 6D on the connecting side having a magnetic south polarity and an inner circle 6C having a magnetic north polarity. Bringing together the respective connecting sides of the two parts 1 and 2 thus not only establishes a connection between the two parts through a drape via a magnetic force, but additionally ensures a reliable alignment of the parts 1 and 2 owing to the different magnetic domains being respectively brought together (4C+6C; 4D+6D) on the connecting surfaces.

Markers such as are shown in the figures may be used in embodiments of the present invention, for example as described in the following:

In accordance with the present invention, a registration device to be used with a medical navigation system may consist of at least three (preferably more, for redundancy purposes) identical marker units 12, each consisting of two parts 1 and 2. The first part 1 of each marker unit is for example fixed to a patient's head, in one embodiment using adhesive tape. The marker units 12 should be well distributed on the object to be registered or referenced, for example the patient's head, in order to form a reference geometry. The first part 1 is formed in such a way that the second part 2 can be fixed on the first part 1, with a drape located between said two parts, wherein they may be fixed inter alia mechanically, magnetically or electrostatically, as shown in the figures and defined above, or by any combination of different techniques. At least the second part 2 of each marker 12 has a reflective surface (or an active light emitter such as an LED) which can be located by a tracking system 30, such that the markers and in particular the reflective surfaces of the second parts 2 serve as patient references.

Registration can be performed by an independent procedure (for example surface matching) or by using the markers. This can be achieved in the same way as with classic fiducials (pointer registration) or by using the positions of the markers determined by the tracking system in order to perform surface matching.

Another option is to enable the first part 1 to be tracked (for example by making it reflective). This would allow independent registration in the non-sterile, non-draped state, and the software could then adapt the registration after draping, when the second parts 2 have been mounted, since the position of the second part 2 with respect to the first part 1 is well defined.

The first part 1 of each marker 12 can be located after registration, for example using a pointer such as a classic fiducial, even though the part 1 is not contained in the object scan. Registration would then be performed by other means (for example surface matching, landmarks, automatically (iCC, REGS, etc.)).

On the other hand, the first part 1 can also be designed as a classical fiducial which is already mounted for the scan. The first part 1 would then for example comprise a pivot point for pointer registration before draping. The second part 2 can also comprise a registration element (pivot point for a pointer) for registering after draping.

Another way of providing a mechanical lock and alignment between the two parts of each marker would be a conical male/female connection or a more complex lock such as a bayonet catch. It may be conceivable in accordance with the present invention to choose a mechanical connection or lock which features drape penetration but is well-covered, for example a small pin, a screw connection or another known or aforementioned type of connection. The parts of the marker may be designed to cover the penetration, such that sterility is maintained. Any combination of these and/or the aforementioned locking or connecting techniques could of course be used within the framework of the present invention.

When performing the method in accordance with the invention, an algorithm is used by the navigation system connected to the tracking system which locates and tracks the markers. For tracking purposes, the algorithm can determine the position of the second part 2 relative to the first part 1 and can take the drape thickness into account. It is also possible to transfer registration from a first-part 1 configuration to a second-part 2 configuration, compensating for deviations determined in the two configurations which occur due to inaccuracies in the connection between the first part 1 and the second part 2, shifts in the skin, camera movement, etc., for example by ignoring the shifted markers. The references tracked may also be only a subset of the available markers, in order to allow better set-up flexibility. In these cases, it is expedient to use more than three markers, i.e. to have a couple of redundant markers.

While it is preferable to use non-invasive means for fixing the first part 1 to the object/patient (adhesives, adhesive tape, glue, an adhesive tape already mounted to the first part 1, etc.), it is generally possible within the framework of the present invention to fix the first part 1 to the object via one or more screws or pins (invasively fixing the first part 1).

The second part 2 may be provided with a special identification, such as a specific shape or color or blinking sequence in order for the system to be able to determine whether it is the first part 1 or the second part 2 which is currently being tracked or detected, such that the navigation system can adapt the referencing algorithm (for example by taking into account the thickness of the drape and the height of the second part 2).

The invention claimed is:

1. A medical tracking marker for localizing or tracking an object by means of a medical tracking system, said marker comprising:
a first part fixable to the object; and
a second part fixably connectable to the first part,
wherein the connection is configured to hold the second part in a predetermined position relative to the first part and the first and second parts comprise interconnecting elements adapted to provide a positionally determinable connection between the first part and the second part while the first part is located under a surgical drape and the second part is located above said surgical drape, with the drape placed between the first and second parts, wherein the first and second parts are provided with two different magnetic or static domains on each surface involved in the connection, thereby securing a predetermined alignment of the first and second parts which are connected without contacting each other, and
wherein the connection is established using forces comprising at least one of magnetic or electrostatic forces.

2. The medical tracking marker according to claim 1, wherein when the first part is connected to the second part the first and second parts are not in direct contact with each other.

3. The medical tracking marker according to claim 2, wherein when connected the interconnecting elements are not in direct contact with each other.

4. The medical tracking marker according to claim 1, wherein when the interconnecting elements are connected said interconnecting elements are spaced apart by at least a distance corresponding to the thickness of a surgical drape, and the connection bridges said distance.

5. The medical tracking marker according to claim 1, wherein when the interconnecting elements are connected the interconnecting elements do not penetrate the drape.

6. The medical tracking marker according to claim 1, wherein when the first and second parts are connected, the first and second parts clamp the drape without penetrating the drape.

7. The medical tracking marker according to claim 6, wherein the interconnecting elements clamp the drape without penetrating the drape.

8. The medical tracking marker according to claim 1, wherein the first and second parts are connected by a positive connection between the interconnecting elements, and the drape is accommodated between said interconnecting elements.

9. The medical tracking marker according to claim 8, wherein the interconnecting elements comprise at least one of a bayonet catch or quarter-turn fastener.

10. The medical tracking marker according to claim 1, wherein the first and second parts are connected by a frictional engagement between the interconnecting elements, and the drape is accommodated between said interconnecting elements.

11. The medical tracking marker according to claim 1, wherein the first part of said marker is non-invasively fixable on the object.

12. The medical tracking marker according to claim 11, wherein the first part comprises an adhesive for fixing the first part to the object.

13. The medical tracking marker according to claim 1, wherein at least one of the first and second parts is provided with a reflective surface detectable by the tracking system.

14. A method of referencing an object using a medical navigation system, wherein a medical tracking marker in accordance with claim 1 is localized or tracked by means of a medical tracking system, and wherein the object is referenced by means of the first part of the marker in a preliminary referencing step, which is later adapted to form a final referencing step for navigation using the second part which has been fixed to the first part in a positionally defined, predetermined manner, wherein the connection is configured to hold the second part in the predetermined position relative to the first part without user intervention.

15. The method according to claim 14, wherein the adapting step compensates for and takes into account a shift in the position of the marker that occurs when the second part is placed on the first part.

16. The method of claim 15, wherein the shift in position is taken into account by ignoring markers which are found to have shifted during the medical navigation.

17. The method of claim 15, wherein compensating includes taking into account at least one of
a thickness of the drape;
a specific shape of the second part;
characteristics of or inaccuracies in the system connecting the parts;
a shift in the skin; or
a movement of the tracking system.

18. A non-transitory computer readable medium comprising computer executable instructions adapted to perform a method in accordance with claim 14.

* * * * *